United States Patent
Gilliam et al.

(10) Patent No.: US 11,039,583 B2
(45) Date of Patent: Jun. 22, 2021

(54) WATERING SYSTEM WITH ADAPTIVE COMPONENTS

(71) Applicant: HUSQVARNA AB, Huskvarna (SE)

(72) Inventors: Sonja Gilliam, Nersingen (DE); Stefan Keller, Neu-Ulm (DE); Thomas Schabel, Burgrieden (DE); Christian Kienzle, Ehingen (DE); Sandra Weiser, Ulm (DE)

(73) Assignee: HUSQVARNA AB, Huskvarna (SE)

( * ) Notice: Subject to any disclaimer, the term of this patent is extended or adjusted under 35 U.S.C. 154(b) by 0 days.

(21) Appl. No.: 15/565,516

(22) PCT Filed: Apr. 10, 2015

(86) PCT No.: PCT/EP2015/057845
§ 371 (c)(1),
(2) Date: Oct. 10, 2017

(87) PCT Pub. No.: WO2016/162085
PCT Pub. Date: Oct. 13, 2016

(65) Prior Publication Data
US 2018/0077882 A1  Mar. 22, 2018

(51) Int. Cl.
*A01G 25/02* (2006.01)
*A01G 25/16* (2006.01)
(Continued)

(52) U.S. Cl.
CPC ........... *A01G 25/167* (2013.01); *A01G 25/02* (2013.01); *A01G 25/165* (2013.01); *B05B 12/02* (2013.01);
(Continued)

(58) Field of Classification Search
CPC .... A01G 25/02; A01G 25/165; A01G 25/167; B05B 12/02; B05B 12/12; G01N 33/246;
(Continued)

(56) References Cited

U.S. PATENT DOCUMENTS 4,176,395 A * 11/1979 Evelyn-Veere ........ A01G 25/16
700/284
5,251,153 A * 10/1993 Nielsen ................. G06F 3/0489
137/551

(Continued)

FOREIGN PATENT DOCUMENTS

CA    2364737 A1 *  5/2003 ............. G01S 19/49
CN    1539261 A    10/2004
(Continued)

OTHER PUBLICATIONS

International Search Report and Written Opinion for International Application No. PCT/EP2015/057845 dated Dec. 4, 2015, all enclosed pages cited.

(Continued)

*Primary Examiner* — Jennifer L Norton
(74) *Attorney, Agent, or Firm* — Burr & Forman, LLP (57) ABSTRACT

A system may include sensor equipment including one or more sensors disposed on a parcel of land, watering equipment disposed on the parcel and configured to selectively apply water to the parcel, and a gateway configured to provide for communication with the sensor equipment and the watering equipment. The gateway may interface between a first network and a second network. The first network may include at least the watering equipment and the sensor equipment. An operator may be enabled to wirelessly communicate with the gateway via the second network. At least one component of the watering equipment or the sensor equipment may be an adaptive component.

19 Claims, 7 Drawing Sheets

(51) Int. Cl.
    *B05B 12/02*     (2006.01)
    *G05B 19/042*    (2006.01)
    *B05B 12/12*     (2006.01)
    *G01N 33/24*     (2006.01)

(52) U.S. Cl.
    CPC ........... *B05B 12/12* (2013.01); *G01N 33/246*
        (2013.01); *G05B 19/042* (2013.01); *G01N*
        *2033/245* (2013.01); *G05B 2219/2625*
        (2013.01)

(58) Field of Classification Search
    CPC ............ G01N 2033/245; G05B 19/042; G05B
        2219/2625
    See application file for complete search history.

(56) References Cited

U.S. PATENT DOCUMENTS

| | | | |
|---|---|---|---|
| 6,437,692 B1* | 8/2002 | Petite | G01D 4/004 340/540 |
| 8,891,317 B2 | 11/2014 | Feki et al. | |
| 9,144,204 B2* | 9/2015 | Redmond | A01G 25/167 |
| 9,307,389 B2 | 4/2016 | Sun et al. | |
| 10,034,421 B2* | 7/2018 | Doughty | G05D 1/0044 |
| 2002/0130781 A1* | 9/2002 | Kroll | E04B 1/70 340/604 |
| 2003/0093159 A1* | 5/2003 | Sieminski | A01G 25/167 700/12 |
| 2003/0230638 A1* | 12/2003 | Dukes | A01G 25/167 239/200 |
| 2004/0015270 A1* | 1/2004 | Addink | A01G 25/16 700/284 |
| 2004/0030456 A1* | 2/2004 | Barlow | A01G 25/165 700/284 |
| 2004/0181315 A1* | 9/2004 | Cardinal | A01G 25/167 700/284 |
| 2004/0225412 A1* | 11/2004 | Alexanian | A01G 25/167 700/284 |
| 2007/0293990 A1* | 12/2007 | Alexanain | A01G 25/16 700/284 |
| 2009/0281672 A1* | 11/2009 | Pourzia | A01G 25/167 700/284 |
| 2010/0241279 A1* | 9/2010 | Samon | A01G 25/16 700/284 |
| 2010/0295672 A1* | 11/2010 | Hyland | H04Q 9/00 340/539.1 |
| 2011/0166701 A1* | 7/2011 | Thacher | A01G 25/00 700/245 |
| 2011/0166715 A1* | 7/2011 | Hoffman | A01B 79/005 700/284 |
| 2012/0041606 A1* | 2/2012 | Standerfer | A01G 25/16 700/284 |
| 2012/0095651 A1* | 4/2012 | Anderson | G05D 1/0274 701/50 |
| 2012/0215366 A1* | 8/2012 | Redmond | A01G 25/167 700/284 |
| 2012/0245740 A1* | 9/2012 | Raestik | G05B 13/027 700/276 |
| 2013/0035774 A1 | 2/2013 | Warren et al. | |
| 2013/0110293 A1 | 5/2013 | Illig | |
| 2013/0131874 A1 | 5/2013 | Shupe et al. | |
| 2013/0207771 A1* | 8/2013 | Ersavas | G05B 15/02 340/3.1 |
| 2014/0018965 A1* | 1/2014 | Pearson | A01G 25/16 700/284 |
| 2014/0039697 A1* | 2/2014 | Weiler | A01G 25/16 700/284 |
| 2014/0224008 A1 | 8/2014 | Hern et al. | |
| 2014/0229025 A1* | 8/2014 | Nickerson | A01G 25/16 700/284 |
| 2014/0236868 A1 | 8/2014 | Cook | |
| 2015/0105921 A1* | 4/2015 | Shupe | A01G 25/16 700/284 |
| 2016/0161940 A1* | 6/2016 | Max | F17D 5/06 700/282 |
| 2016/0198644 A1* | 7/2016 | Lameli | G05B 19/042 700/284 |
| 2016/0219805 A1* | 8/2016 | Romney | A01G 25/16 |
| 2019/0090440 A1* | 3/2019 | Gungl | A01G 25/167 |
| 2019/0159411 A1* | 5/2019 | Gungl | A01G 25/167 |
| 2019/0254242 A1* | 8/2019 | Allen | A01G 25/02 |
| 2019/0258267 A1* | 8/2019 | Hahn | A01D 34/008 |
| 2019/0261585 A1* | 8/2019 | Weiler | G05B 19/0426 |
| 2019/0297798 A1* | 10/2019 | Levine | G01W 1/00 |

FOREIGN PATENT DOCUMENTS

| | | | |
|---|---|---|---|
| CN | 101149867 A | 3/2008 | |
| CN | 101155090 A | 4/2008 | |
| CN | 101389107 A | 3/2009 | |
| CN | 101569281 A | 11/2009 | |
| CN | 101642039 A | 2/2010 | |
| CN | 201448993 U | 5/2010 | |
| CN | 101806925 A | 8/2010 | |
| CN | 101869046 A | 10/2010 | |
| CN | 101999306 A | 4/2011 | |
| CN | 102037888 A | 5/2011 | |
| CN | 102506941 A | 6/2012 | |
| CN | 102572721 A | 7/2012 | |
| CN | 202419936 U | 9/2012 | |
| CN | 102771358 A | 11/2012 | |
| CN | 102788183 A | 11/2012 | |
| CN | 202857464 U | 4/2013 | |
| CN | 103070057 A | 5/2013 | |
| CN | 203148876 U | 8/2013 | |
| CN | 203501580 U | 3/2014 | |
| CN | 103718929 A | 4/2014 | |
| CN | 103871252 A | 6/2014 | |
| CN | 103875508 A | 6/2014 | |
| CN | 103999001 A | 8/2014 | |
| CN | 203872715 U | 10/2014 | |
| CN | 204062483 U | 12/2014 | |
| CN | 204141852 U | 2/2015 | |
| DE | 102011084594 A1 | 4/2013 | |
| EP | 2342965 A1 | 7/2011 | |
| JP | 2002-233255 A | 8/2002 | |
| JP | 2012-147753 A | 8/2012 | |
| TW | 201442616 A | 11/2014 | |
| WO | WO-0101752 A2 * | 1/2001 | ............ A01G 25/16 |
| WO | WO-2014007729 A1 * | 1/2014 | |
| WO | 2014109889 A2 | 7/2014 | |
| WO | 2015/022654 A1 | 2/2015 | |
| WO | 2015/022672 A3 | 2/2015 | |

OTHER PUBLICATIONS

Chapter II International Preliminary Report on Patentability for International Application No. PCT/EP2015/057845 dated Jul. 4, 2017, all enclosed pages cited.
Corrected Chapter II International Preliminary Report on Patentability for International Application No. PCT/EP2015/057845 dated Aug. 1, 2017, all enclosed pages cited.
Second Written Opinion of the International Preliminary Examining Authority for International Application No. PCT/EP2015/057845 dated Mar. 1, 2017, all enclosed pages cited.

* cited by examiner

WATERING SYSTEM WITH ADAPTIVE COMPONENTS

TECHNICAL FIELD

Example embodiments generally relate to intelligent systems and, more particularly, relate to a system for intelligent watering that includes components configured to adaptively react to environmental/situational factors.

BACKGROUND

Grounds care maintenance tasks may include lawn care and/or gardening tasks related to facilitating growth and manicuring the lawns or gardens that hopefully prosper as a result of those efforts. Facilitating growth has commonly required individuals to focus routine attention on ensuring growing conditions are appropriate for the vegetation being grown, and on providing the necessary care and grooming tasks to further enhance growth.

As technological capabilities have improved, various devices or sensors have been developed that are capable of employment to monitor various aspects of growing conditions. Gardeners have therefore been enabled to employ the sensors or devices in specific locations to monitor and correct, if needed, the growing conditions. However, even with the improvement of monitoring devices or sensors, gardeners are still often required to employ a high degree of manual interaction to place and/or operate the devices or sensors.

BRIEF SUMMARY OF SOME EXAMPLES

Some example embodiments may therefore provide a capability for intelligent control or management of a number of assets in connection with yard maintenance with the assistance or inclusion of a gateway that connects in-home communication networks to a garden network. Thus, for example, sensor equipment and watering equipment operation may be adaptively coordinated for efficient gardening and lawn care.

In an example embodiment, a system for intelligent control or management of a number of assets in connection with yard maintenance is provided. The system may include sensor equipment including one or more sensors disposed on a parcel of land, watering equipment disposed on the parcel and configured to selectively apply water to the parcel, and a gateway configured to provide for communication with the sensor equipment and the watering equipment. The gateway may interface between a first network and a second network. The first network may include at least the watering equipment and the sensor equipment. An operator may be enabled to wirelessly communicate with the gateway via the second network (e.g., via an app). At least one component of the watering equipment or the sensor equipment may be an adaptive component.

Some example embodiments may improve the ability of operators to maximize the beauty and productivity of their yards and gardens, but do so in a simple and user friendly way.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. Furthermore, as used herein, the term "or" is to be interpreted as a logical operator that results in true whenever one or more of its operands are true. Additionally, the term "yard maintenance" is meant to relate to any outdoor grounds improvement or maintenance related activity and need not specifically apply to activities directly tied to grass, turf or sod care. Thus, yard maintenance should be appreciated to encompass gardening, lawn care, combinations thereof, and/or the like. As used herein, operable coupling should be understood to relate to direct or indirect connection that, in either case, enables functional interconnection of components that are operably coupled to each other.

Example embodiments may provide an intelligent system for monitoring and/or maintaining yard conditions (i.e., lawn and/or garden conditions) at any of what may potentially be a number of locations throughout a particular parcel, and allowing the operator to interface with devices within the system in a flexible way. Moreover, the devices of the system may be coordinated in their activities and/or may be configured to adapt to their environment or at least to the current conditions or stimuli that are present in their environment. In some cases, the operations conducted and/or monitoring may be accomplished with the assistance of a mobile asset such as a robotic rover. In this regard, for example, the system may utilize a communication network that gathers information on growing conditions from sensor equipment for association of the information with the areas from which the information was gathered. The system may also employ an interface mechanism that allows the operator to have a great deal of flexibility with remotely controlling various components of the system and programming such components via processing circuitry at each respective component. Programming may therefore be coordinated remotely, but at least some of the programming may also be stored locally so that the system can operate with or without connectivity. In some cases, the connectivity aspects of the system may utilize home network components and wide area network components (e.g., the internet), but may also include a gateway that is configured to interface between the deployed components (e.g., components in the yard/garden or otherwise related to yard maintenance) and the home network/wide area network components. As mentioned above, the processing aspects may be distributed between local and remote management components so that some aspects of yard maintenance may utilize remote assets or at least incorporate information available from abroad, while other aspects can be managed locally. In any case, adaptability and ease of interface and control are characteristics of the system that are improved by employing example embodiments.

The system may therefore employ any combination of fixed and/or mobile assets that gather data that relates to specific segments of the parcel that may correspond to respective different areas. The specific segments may have different types of plants therein, and therefore may optimally have different growing conditions desirable in connection with each respective one of the segments. The owner/operator may program operating instructions to guide the deployed components relative to operations in the specific segments, which may be referred to as "zones." In some cases, the processing circuitry may be equipped to allow the user to define specific operating parameters and the system may then adapt to the current conditions to operate according to the operating parameters. Given that internet connectivity is possible, in some cases, the system may be employed to correlate desirable growing conditions to an identified plant species based on stored information associated with each plant species from a database or online resource. Accordingly, each zone may have corresponding growing condition parameters associated therewith, and the user can see the growing condition parameters relative to the various areas and program operation of system components accordingly relative to maintaining desired growing conditions (e.g., any or all of moisture level, temperature, lighting level, pH, and/or the like) for the corresponding zone. In some cases, schedules among deployed components may be deconflicted or otherwise organized to prevent damage to components, ineffective use of resources, or efficiency reducing behaviors. The deployed components associated with the zones may provide the operator with reports and/or warnings via the gateway to enable the operator to intercede in certain situations, or the components may simply respond and inform the operator of their responses via the gateway.

Figure 1:
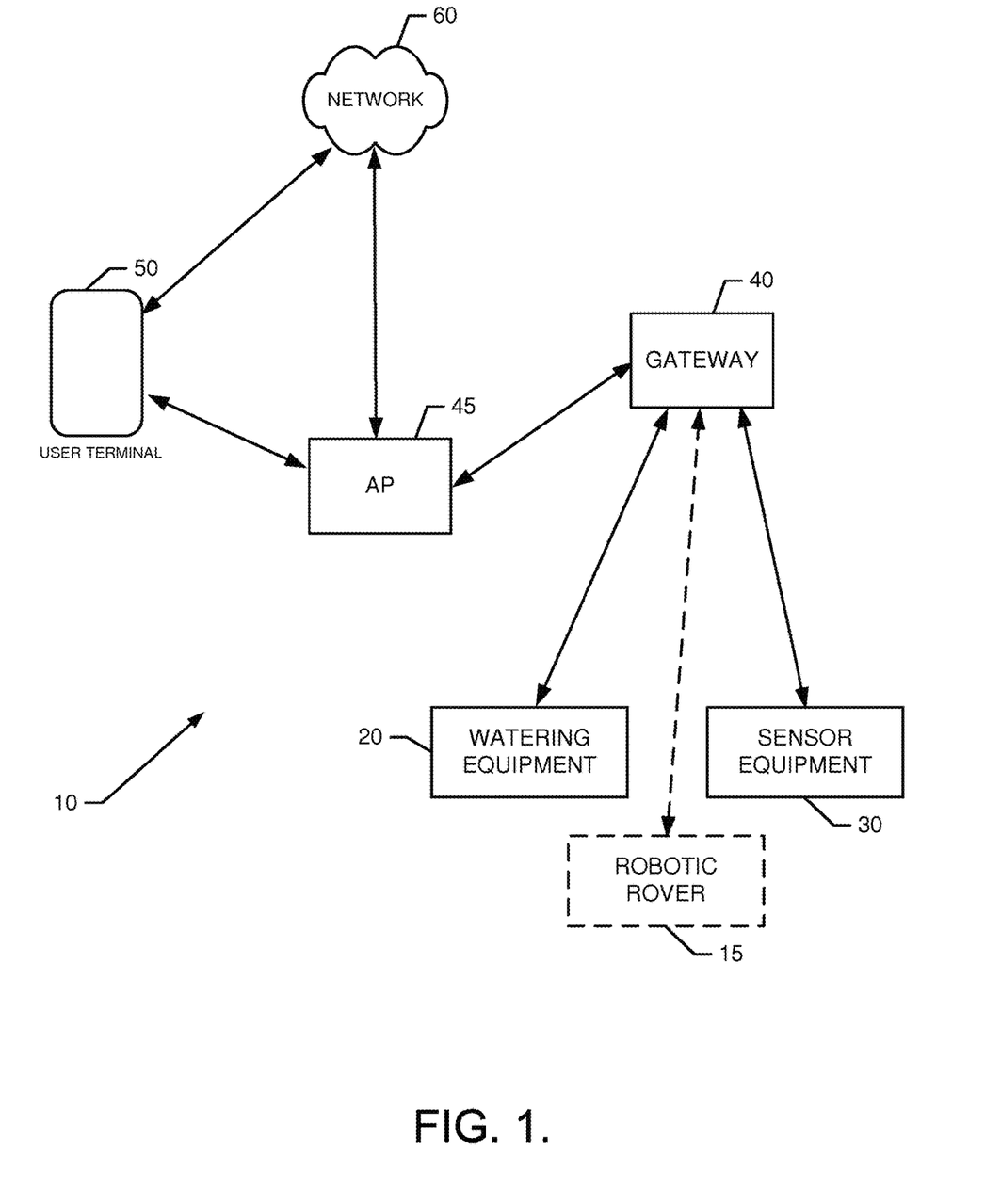
FIG. 1 illustrates a block diagram of a system in accordance with an example embodiment.

FIG. 1 illustrates a block diagram of a system 10 that may be employed to accomplish the basic operations described above in accordance with an example embodiment. Within the context of FIG. 1, it should be appreciated that certain tasks, like grass cutting, chemical application, visual monitoring and/or the like may be performed by a robot or robotic rover 15. Because the system could operate without the robotic rover 15, the robotic rover 15 is shown in dashed lines in FIG. 1. Robots or other devices could also be engaged to perform certain other yard maintenance tasks such as raking, fertilizing, lighting, watering, wildlife dispersion and/or the like.

Other tasks, like lawn watering, may be performed by sprinkler heads and/or a watering computer that interfaces therewith. The sprinkler heads may be attached to hoses and the watering computer may provide a mechanism by which to control the turning on/off of water application at the respective sprinkler head locations by providing a central shut off valve for the hoses. The hoses, sprinkler heads and/or watering computer may together form watering equipment 20.

Meanwhile, various sensors may be employed by insertion of such sensors into soil for monitoring soil or other growing conditions (e.g., lighting levels, moisture levels, pH, temperature, video or image data, etc.). These sensors may therefore be understood to take various forms within the system 10. However, generally speaking, the sensors may have connectivity to the system 10 in order to enhance operation of system components on the basis of the soil and/or growing condition information gathered by the sensors. Regardless of the specific configuration or placement paradigm, the various sensors may represent sensor equipment 30, as described above.

The sensor equipment 30, and in some cases also one or more of the devices that comprise the watering equipment 20, may be in communication with a gateway 40 via wired or wireless connections. The gateway 40 may subsequently have wired or wireless connection to an access point (AP) 45, which may be directly or indirectly connectable to a user terminal 50. The AP 45 may be a router of a home network of the operator. In some cases, direct connection of the AP 45 to the user terminal 50 may be provided via short range wireless communication methods (e.g., Bluetooth, WiFi and/or the like). Indirect connection of the AP 45 to the user terminal 50 may occur via a network 60. The network 60 may be a data network, such as a local area network (LAN), a metropolitan area network (MAN), a wide area network (WAN) (e.g., the internet), a wireless personal area network (WPAN), and/or the like, which may couple devices (e.g., the deployed components) to devices such as processing elements (e.g., personal computers, server computers or the like) and/or databases such as the user terminal 50. Communication between the network 60 and other devices of the system 10 may be accomplished by either wireline or wireless communication mechanisms and corresponding communication protocols. As such, for example, some or all of the sensors of the sensor equipment 30, the watering equipment 20 and/or the robotic rover 15, may be connected to the user terminal 50 by wire and/or be wireless communication means.

It should also be appreciated that although the robotic rover 15 is illustrated separately in FIG. 1, the robotic rover 15 may act as one or both of a piece of sensor equipment 30 or a piece of watering equipment 20. However, given the ability of the robotic rover 15 to act as either or both of a piece of sensor equipment 30 or a piece of watering equipment 20 and the ability of the robotic rover 15 to perform other tasks (e.g., grass cutting) in combination with or independent of the sensor equipment 30 and the watering equipment 20, the robotic rover 15 is shown separately in FIG. 1.

The gateway 40 may be a translation agent configured to interface with any or all of the deployed components via wired or wireless communication. In some embodiments, the gateway 40 may include a high performance antenna to enable the gateway 40 to communicate wirelessly with deployed components via an 868 mHz radio link (e.g., a first wireless link). However, other radio links may be employed in other cases. The first wireless link, and the components connected thereby, may be part of a first network (e.g., a garden network) or deployed component network that extends outdoors. Components internal to the house or business, and extending to and between the user terminal 50 may form a second network. As such, the gateway 40 may be a translation agent between the first and second networks. The gateway 40 may be an aggregation point and communications center for communications in both networks.

As such, the gateway 40 may be provided within the home or otherwise indoor environment of the operator, and still wirelessly communicate with the deployed components (via the first wireless link) to translate instructions thereto from the operator, which may be provided via a second wireless link to the AP 45. In an example embodiment, the wireless communications may be secured by employing encryption or other security techniques. The gateway 40 may also provide secure cloud data storage through connection to the network 60 (e.g., via the AP 45). In some examples, the first and second wireless links may be different wireless links that employ different communication protocols and/or frequencies.

The gateway 40 may also provide the ability for each of the deployed components to be monitored, controlled, programmed or otherwise interfaced with by an operator using the user terminal 50. In particular, in some cases, the user terminal 50 may be configured to execute an application (or app) that is tailored to providing an easy setup and/or easy to use interface for interaction with the gateway 40 (and the corresponding deployed components that are reachable through the gateway 40). The user terminal 50 may therefore be a smartphone or other mobile terminal, or a laptop, PC, or other computing/communication device. As such, the user terminal 50 may include processing circuitry that is enabled to interface with corresponding processing circuitry of the gateway 40 and/or the deployed components to program, control or otherwise interact with the deployed components in a manner described in greater detail below.

The interaction between the user terminal 50 and the gateway 40 to facilitate programming of, control of, or interaction with the deployed components may create an interactive and fully connectable garden system for irrigation and/or mowing control/coordination. The app that may be executed at the user terminal 50 may be configured for control of any or all of the deployed components on a real time or programmed basis. The resulting system may be a holistic and connected automatic garden system. Moreover, the connection to content on the internet via network 60 may allow educational content to be integrated into the system's operation to provide operators with an improved interface and more control over gaining full satisfaction of their gardening experience.

Figure 2:
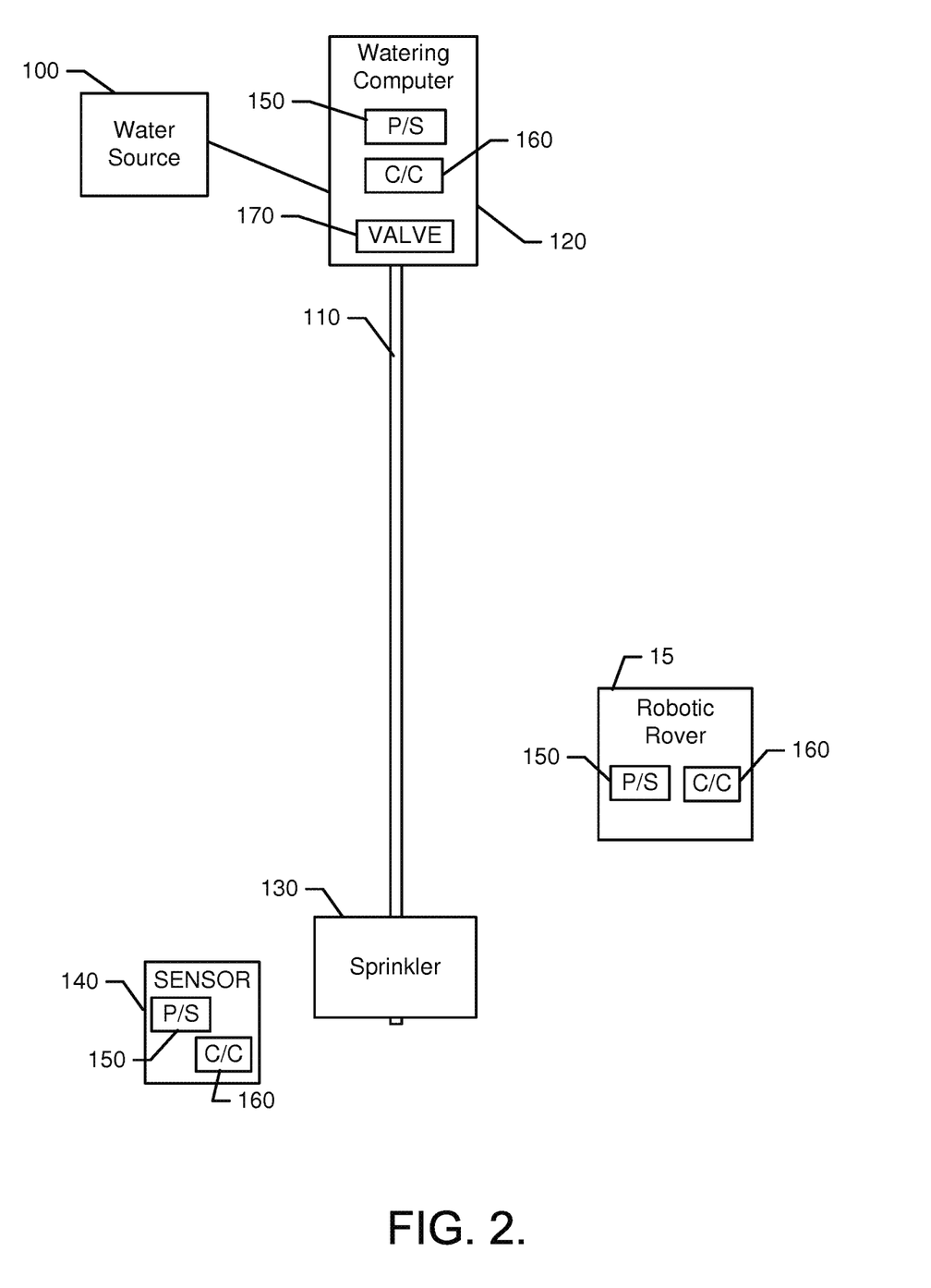
FIG. 2 illustrates a block diagram of deployed components of the system according to an example embodiment.
Figure 3:
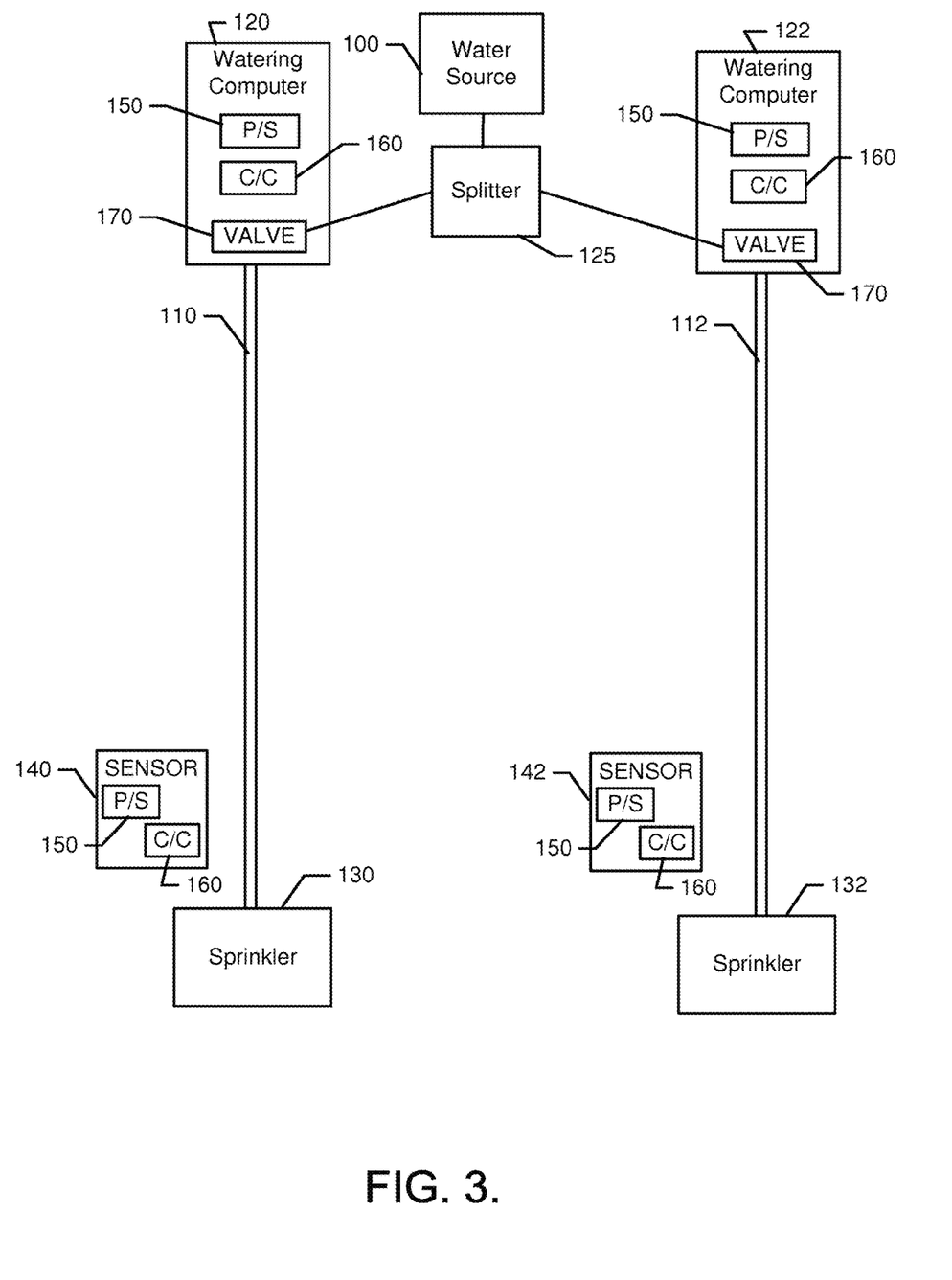
FIG. 3 illustrates the deployed components duplicated for multiple water lines in accordance with an example embodiment.

FIGS. 2 and 3 illustrate a water migration path that may be practiced in connection with an example embodiment. However, it should be appreciated that some of the components may be removed in simpler example embodiments, and some components may be added to provide more complex architectures in other example embodiments. Thus, the examples of FIGS. 2 and 3 not provided to be limiting in relation to the components included in the system, but merely to show various examples of some components that may be included in one example system. Moreover, it should be appreciated that FIG. 3 is merely shown to illustrate one way in which multiple water delivery lines can be provided to service a parcel or yard. The fact that FIG. 3 only shows two water lines is not meant to imply that example embodiments may only work with two lines. To the contrary, example embodiments may be practiced with any number of lines, and with separate and/or different water sources. Moreover, the lines may be in-ground lines that are part of an installed irrigation system, or movable hoses that are typically provided above ground.

Referring now to FIGS. 2 and 3, a water source 100 may be used to charge a first water line 110 via a watering computer 120. In some cases (see FIG. 3), the water source 100 may also charge a second water line 112 via a second watering computer 122. The first and second water lines 110 and 112 may each be a flexible water hose or garden hose. The first and second watering computers 120 and 122 may each be one of the deployed components that forms one component of the watering equipment 20 of FIG. 1. The first and second watering computers 120 and 122 may be directly attached to the water source 100 such that the water source 100 is a tap or spigot to which the pressurized water supply of a house or other structure is supplied. However, in other examples, a hose or other connector may be provided between the first and second watering computers 120 and 122 and the water source 100. An example of such other connector is shown in FIG. 3, which illustrates an example in which a splitter 125 is provided to split water between the first and second watering computers 120 and 122 and the first and second water lines 110 and 112 that may otherwise be identical or similar to each other in their makeup and operation. It should also be appreciated that the splitter 125 may have the ability to interface with the gateway 40 in some embodiments. Thus, wired or wireless control of any number of irrigation lines may be possible.

In an example embodiment, one or more sprinklers (e.g., a first sprinkler 130 and a second sprinkler 132) may receive water from the first water line 110 and second water line 112, respectively. The first water line 110 may be selectively charged under control of the first watering computer 120 to provide water for spraying from the first sprinkler 130. Likewise, the second water line 112 may be selectively charged under control of the second watering computer 122 to provide water for spraying from the second sprinkler 132. When the first water line 110 is charged, the first sprinklers 130 may be provided with pressurized water that is distributed there through, and the second sprinkler 132 may be similarly provided with water responsive to operation of the second watering computer 122. The first and second sprinklers 130 and 132 may typically be components that are not provided with any local intelligence. Instead, the first and second sprinklers 130 and 132 may only be controllable via operation of the first and second watering computers 120 and 122, respectively, to turn on and off watering functions. However, it is possible that the first and second sprinklers 130 and 132 could have intelligent components and/or control aspects provided therein in some cases.

One or more sensors (e.g., first sensor 140 and second sensor 142) may also be provided at various locations in the parcel that is served by the sprinklers to detect or sense conditions proximate to the corresponding sensors. The first and second sensors 140 and 142 may each correspond to a respective one of the first and second sprinklers 130 and 132, and the app at the user terminal 50 may be configured to note such correspondence so that information received from a respective one of the first or second sensor 140 or 142 can be correlated to actions that may be ordered to the first watering computer 120 or the second watering computer 122, if needed, based on the information.

In some examples, some of the deployed components may include a power supply (P/S) 150 that is local to the corresponding ones of the deployed components. The P/S 150 f each component may be a battery or battery pack. Each powered one of the deployed components may also include communication circuitry (C/C) 160 that includes processing circuitry for controlling each respective component and an antenna for enabling the deployed components to communicate with the gateway 40 via the first wireless link (or alternatively via a wired connection). The robotic rover 15 may also be an example of the deployed components, and thus the robotic rover 15 may also include the P/S 150 and the C/C 160. However, it should be appreciated that the various power supply and communication circuitry components may have different scale, structure and configuration features.

The first and second watering computers 120 and 122 may each further include a valve 170, which may be operated to respectively isolate and operably couple the water source 100 from/to the first water line 110 and/or the second water line 122, respectively. The valve 170 may be operated based on instructions received through the gateway 40 or based on schedule information stored or otherwise accessible via the C/C 160 of the first or second watering computers 120 or 122. The first and second watering computers 120 and 122 may provide convenience to operation of the system 10 since the first and second watering computers 120 and 122 can be controlled from anywhere and/or at anytime via the app at the user terminal 50 by programming a schedule or manually directing operation of the first and second watering computers 120 and 122 at the user terminal 50. However, in some cases, the app can also be used to program the watering computer 120 for automatic operation of the valves 170 based on sensor data received from the first or second sensor 140 or 142.

Figure 4:
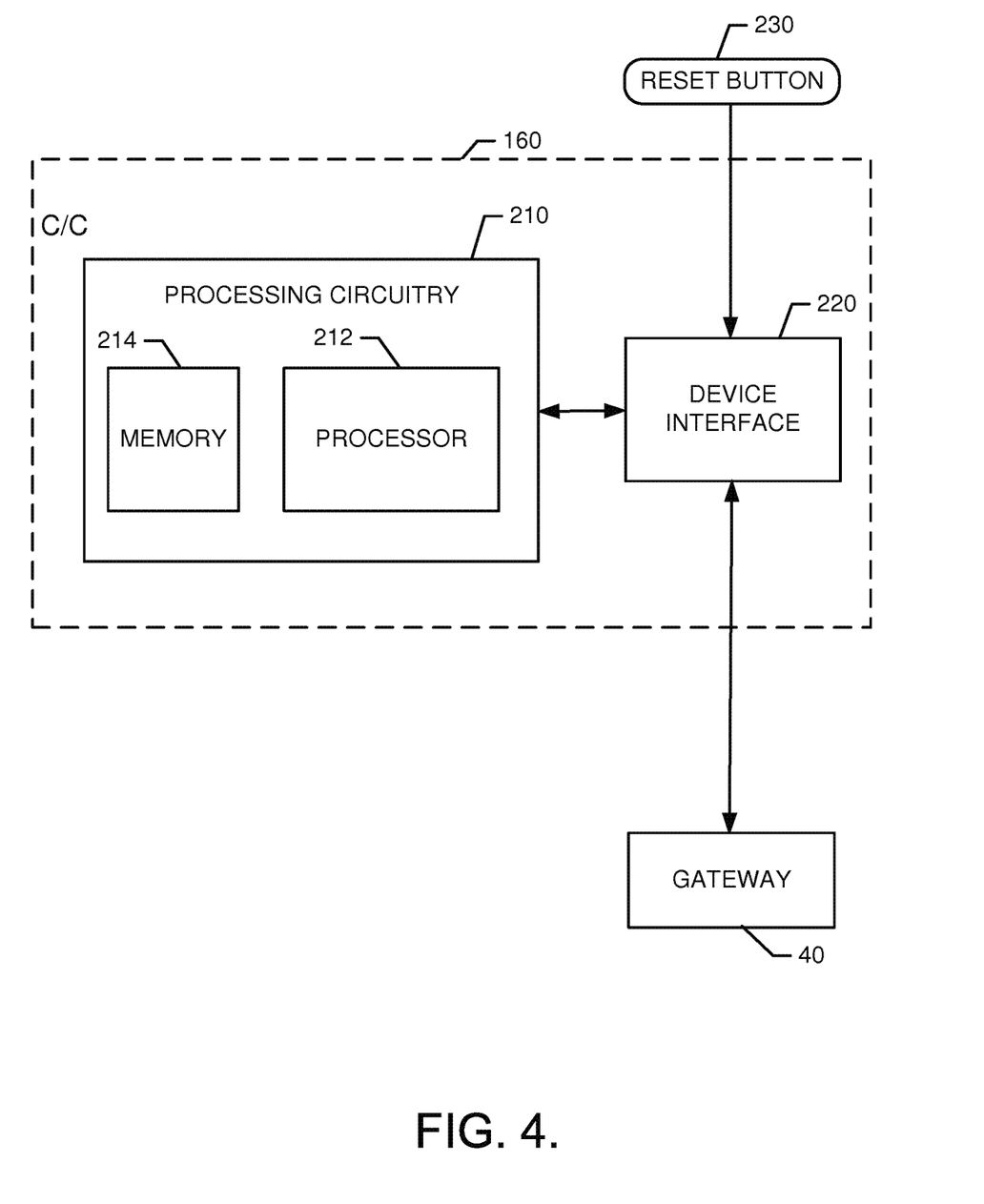
FIG. 4 illustrates a block diagram of processing circuitry that may be employed in the deployed components according to an example embodiment.

In an example embodiment, the C/C 160 may include processing circuitry 210, as shown in FIG. 4. The processing circuitry 210 that may be configured to perform data processing, control function execution and/or other processing and management services according to an example embodiment of the present invention. In some embodiments, the processing circuitry 210 may be embodied as a chip or chip set. In other words, the processing circuitry 210 may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The processing circuitry 210 may therefore, in some cases, be configured to implement an embodiment of the present invention on a single chip or as a single "system on a chip." As such, in some cases, a chip or chipset may constitute means for performing one or more operations for providing the functionalities described herein.

In an example embodiment, the processing circuitry 210 may include one or more instances of a processor 212 and memory 214 that may be in communication with or otherwise control a device interface 220. As such, the processing circuitry 210 may be embodied as a circuit chip (e.g., an integrated circuit chip) configured (e.g., with hardware, software or a combination of hardware and software) to perform operations described herein. In some embodiments, the processing circuitry 210 may communicate with internal electronic components of the first and second watering computers 120 and 122, the first or second sensors 140 and 142 and/or the robotic rover 15, and enable communication externally with other components.

The device interface 220 may include one or more interface mechanisms for enabling communication with other devices via the gateway 40. In some cases, the device interface 220 may be any means such as a device or circuitry embodied in either hardware, or a combination of hardware and software that is configured to receive and/or transmit data from/to the gateway 40 by virtue of the device interface 220 being capable of sending and receiving messages via the gateway 40. In some example embodiments, the device interface 220 may provide interfaces for communication of components of or external to the system 10 via the gateway 40. If the C/C 160 is for a sensor, the device interface 220 may further interface with a sensor (e.g., a temperature sensor, a pH sensor, a light sensor, a moisture sensor and/or the like) to obtain sensor data for communication to other devices (e.g., the watering computers). Meanwhile, if the C/C 160 is for a watering computer, the device interface 220 may provide interfaces to other onboard components (e.g., a user interface including lights and a main button as described below).

The processor 212 may be embodied in a number of different ways. For example, the processor 212 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry in the form of processing circuitry 210) capable of performing operations according to embodiments of the present invention while configured accordingly. Thus, for example, when the processor 212 is embodied as an ASIC, FPGA or the like, the processor 212 may be specifically configured hardware for conducting the operations described herein. Alternatively, as another example, when the processor 212 is embodied as an executor of software instructions, the instructions may specifically configure the processor 212 to perform the operations described herein.

In an example embodiment, the processor 212 (or the processing circuitry 210) may be embodied as, include or otherwise control the C/C 160. As such, in some embodiments, the processor 212 (or the processing circuitry 210) may be said to cause each of the operations described in connection with the C/C 160 (and corresponding distributed component with which the C/C 160 is associated) by directing the C/C 160 to undertake the corresponding functionalities responsive to execution of instructions or algorithms configuring the processor 212 (or processing circuitry 210) accordingly. As an example, the C/C 160 of the sensors may be configured to detect environmental parameters (e.g., sensor data) and report the sensor data via the first wireless link to the gateway 40 (and ultimately to the app on the user terminal 50 or to storage in the cloud via the network 60). In some cases, the C/C 160 of the sensors may be configured to determine a difference between a prior set of sensor data (e.g., the magnitude of a previous sensor measurement) and the current set of sensor data (e.g., the magnitude of a most recent sensor measurement). The amount of difference may then be used to determine whether or not the sensor will report the current set of sensor data. If the difference is small (e.g., less than a threshold amount) the sensor may not report the new value. However, if the difference is large enough (e.g., larger than the threshold amount), then the sensor may report the new value. As such, the C/C 160 of the sensors may be configured to perform battery conservation techniques relative to reporting of sensor data. The C/C 160 of the sensors may also be configured to otherwise report (or make a determination on whether to report based on the criteria discussed above) sensor data on a given schedule or responsive to certain activities or events. When a trigger event (e.g., temporal or action based trigger) occurs, the C/C 160 of the sensor may make a determination of the current sensor data and decide whether or not to report the sensor data.

The C/C 160 of the watering computers may be configured to control the operation of the valve 170 on the basis of schedule information stored locally in the memory 214 of the C/C 160. The C/C 160 of the watering computers may also allow modifications to the schedule, other programming operations, and/or the real-time taking of control over the position of the valve 170. Thus, for example, the operator may be enabled to remotely monitor current valve 170 position and/or program settings and make modifications to either. In some embodiments, the C/C 160 of the watering computers may be programmed to water when sensor data falling within or exceeding certain ranges or thresholds is received. Thus, for example, if the sensor data indicates that soil moisture is below a given threshold, the watering computers may be configured to open the valve 170 to deliver water to the sprinklers.

The C/C 160 of the robotic rover 15 may be configured to control the travels and operations of the robotic rover 15. Moreover, the C/C 160 of the robotic rover 15 may allow the gateway 40 to grant user access to modification of the schedule of operations of the robotic rover 15 and/or to take real-time control over various operations of the robotic rover 15. In an example embodiment, the app at the user terminal 50 may be employed to coordinate and/or de-conflict watering schedules and mowing schedules. Additionally or alternatively, if the operator makes a modification to a schedule or takes real-time control of one or more components, the app at the user terminal 50 may provide alerts to indicate that the proposed changes to the schedule or current operations may be problematic, or may prevent the making of such changes. Thus, for example, if the robotic rover 15 is mowing in an area in which a sensor indicates a low soil moisture value that would normally trigger opening of the valve 170 via the watering computer's programming, an alert may be provided to indicate that the robotic rover 15 should have its operations changed, or the opening of the valve 170 may be delayed.

In an example embodiment, the electronic deployed components (e.g., components having a P/S 150) may further include a reset button 230 provided at a secure portion thereof. In some cases, the reset button 230 may be provided in or near a battery compartment of the corresponding device. The reset button 230 may be used to insert a reset condition that may trigger different functionalities through the programming of the processing circuitry 210 for corresponding different situations and/or actuation methods. For example, a short press of the reset button 230 may cause the corresponding device to go into a pairing mode. Once in the pairing mode, the device may be detectable by the gateway 40 and/or other devices for a given period of time. The app on the user terminal 50 may be used to detect the device in pairing mode and, once detected, the app may also be used to pair the device to another device (e.g., of the first network- the deployed component network). The gateway 40 and the C/C 160 of the corresponding devices may then be capable of communication with each other on a continuous, event driven or scheduled basis via the first wireless link. Thus, for example, the first sensor 140 may be configured to provide sensor data to the first watering computer 120 (e.g., via the gateway 40). In some cases, the first sensor 140 may be paired with the first watering computer 120 via a setup procedure and communicate thereafter on a schedule or an activity/event driven basis. In some cases, simple replacement or insertion of a battery to power up the device may be an additional or alternative method by which to initiate the pairing mode.

In some cases, a long press of the reset button 230 (e.g., greater than five seconds of holding the reset button 230) may result in returning the device to factory settings. As such, contents of the memory 214 may be cleared or otherwise reset to initial settings or conditions. Other functions may also or alternatively be provided. Moreover, some devices may have additional buttons or operable members. For example, the first watering computer 120 may have a main button on a housing of the first watering computer 120 as described in greater detail below.

Communication between the gateway 40 and the sensors or watering computers may occur for pairing purposes and to facilitate the operational activities for which the system 10 is ultimately configured. Thus, for example, the operator may use the app at the user terminal 50 to connect to the gateway 40 and may be provided with one or more control console or interface screens that provide options for interacting with deployed components and/or for programming the deployed components. In some cases, initial setup of the system may be facilitated by placing individual deployed components (either sequentially or simultaneously) in a pairing mode. The deployed components are then discoverable via the first wireless link and can be added to the first network. Once added to the first network, the deployed components are considered to be assets of the first network that can be interacted with/programmed and/or the like. The deployed components can then be paired with each other and configured for individual and/or cooperative functional performance.

In an example embodiment the first watering computer 120 may be paired with the second watering computer 122, with the robotic rover 15 and/or the first sensor 140. When the first watering computer 120 is paired with and connected to the first sensor 140, the operator may have options provided (e.g., via the app) to select instructions or scheduling options for intelligent irrigation. The first watering computer 120 may therefore be instructed regarding the specific stimuli that may be received from the first sensor 140 to trigger opening the valve 170. Additionally, the first watering computer 120 may be provided with (e.g., in the memory 214) a schedule or listing of event triggers which cause the first watering computer 120 to "ping" or otherwise reach out to the first sensor to initiate communication to receive sensor data. Based on the sensor data received (e.g., if certain threshold parameters are reached or not), the valve 170 may be opened.

When the first watering computer 120 is paired with and connected to the robotic rover 15, automatic coordination of schedules may be accomplished at least relative to ensuring that mowing and watering are not conducted in the same area at the same time. The app on the user terminal 50 may ensure that scheduling of mowing during watering (or vice versa) is not possible. However, given that the operator can take control of the watering computers and/or the robotic rover 15 to initiate operations, the app on the user terminal 50 may further prevent any attempts to initiate operations of watering computers or the robotic rover 15 in real-time when the other is also operating in the same area.

When the first watering computer 120 is paired with and connected to the second watering computer 122, watering schedules or operations can be coordinated to manage or prevent under-pressure situations. For example, if the first and second watering computers 120 and 122 are connected to the splitter 125, as shown in FIG. 3, it may be possible for water pressure to be insufficient to effectively charge both the first water line 110 and the second water line 112 at the same time. Thus, by allowing the first and second watering computers 120 and 122 to be in communication with each other, operations of one may be communicated to the other (e.g., via the gateway 40) so that the second watering computer 122 will not open its valve 170, while the first watering computer 120 is currently engaged in watering operations.

The deployed components of various example embodiments may be adaptive to various conditions or situations. Moreover, the adaptive nature of the deployed components may be provided as a programmable feature, where the operator can use the user terminal 50 to program specific adaptive behaviors that are adjustable parameters, relationships or responses. In the context of some examples, the programmable feature should be understood to be remotely programmable (i.e., programmable from the app and/or the user terminal 50 remote from the component being programmed) via the gateway 40. In other examples, the adaptive nature of the deployed components may be provided as a default feature. Thus, the adaptive capabilities of the deployed components may either be dependent upon connectivity (e.g., connectivity dependent) for remote programming, or may be connectivity independent (e.g., default programming that exists or is instituted when there is no connectivity or responsive to a loss of connectivity.

In some embodiments, battery power levels may be communicated to the gateway 40 and signal strength values relating to communication with the sensors and/or watering computers may also be determined at the gateway 40. This information (along with sensor data) may be provided to the app at the user terminal 50 to alert the operator when battery power is low, or signal strengths are low. Battery replacement and/or sensor repositioning may then be undertaken to improve the situation. As mentioned above, in some cases, the sensor may also adaptively respond to its surroundings to trigger reports. In an example embodiment, the water computer may attempt to ping the sensor via the gateway 40 to trigger a report of sensor data. However, the sensor may be configured (e.g., via the C/C 160) to determine the amount of change in the requested parameter before deciding whether to respond to the ping. In some embodiments, a change of at least a specific amount or percentage (e.g., 5%) may be required before the sensor will report sensor data via wireless transmission. Since wireless transmission consumes more power than internal operation (e.g., to determine the amount of change and current sensor data), by saving several transmission cycles when there is little data change, battery life can be substantially extended. When a ping is sent and no response is received, the last value received may be substituted and communicated to the operator (e.g., via the app).

The operator can wake up the watering computers and/or sensors by sending a ping or wake up message to either component via the app. The wake up message may be used to see if the devices are still reacting and active, or to request specific data from or initiate actions at such components in real time. Moreover, in some cases, the operator can send a wakeup, or setup signal to have the corresponding device beacon for at least a predetermined amount of time (e.g., three minutes). During this time, the devices may be positioned and the operator may check the app to see what signal strength is detected by the gateway 40. The operator can therefore position the devices in real time and make sure that the position in which a device is currently located is a good location from the perspective of its ability to communicate with the gateway 40.

In some embodiments, one or more of the deployed components may further include frost warning capability. In particular, since the watering computers typically have pressurized water proximate to the valve 170, it should be appreciated that freezing of water in the body of the watering computers may be destructive to the valve 170. Accordingly, the C/C 160 of one or more components (especially the watering computers) may be configured to identify situations where there is a potential for frost that may damage the watering computers. In some embodiments, if the temperature reaches a predetermined threshold distance from the freezing point (e.g., 5 degrees C., or 10 degrees F.), an alert may be issued (e.g., through the app at the user terminal 50) to warn the operator that the watering computer (and/or sensors) should be brought in to avoid damage. The predetermined threshold may be a factory setting, or may be set by the operator. However, in either case, the ability to identify a present temperature condition to alert the operator of a possible frost event is another example of how the deployed components may be configured (by operator program or by default) to be adaptive relative to their surroundings and/or circumstances.

Another example of the adaptability of the deployed components relates to the inability to connect to the first network or a loss of connection to the first network. For example, although the watering schedules could be maintained in the cloud, on the user terminal 50 or elsewhere, in some cases, the watering schedule (or at least a portion thereof) may be stored locally at the watering computers. For example, the memory 214 may be configured to record at least the last water schedule information employed. Thus, power is lost at the gateway 40 or at another system component that thereby renders connectivity impossible, the first and second watering computers 120 and 122 may each store at least the information indicative of their respective last watering schedules. Thus, for example, if the first watering computer 120 opened the valve 170 at 1300 and shut the valve at 1305, while the second watering computer 122 opened its valve 170 at 1305 and closed it at 1318, if no connection to the watering schedule can be achieved, or if connectivity is lost, each of the first and second watering computers 120 and 122 will continue to water on the previously provided schedule.

Figure 5:
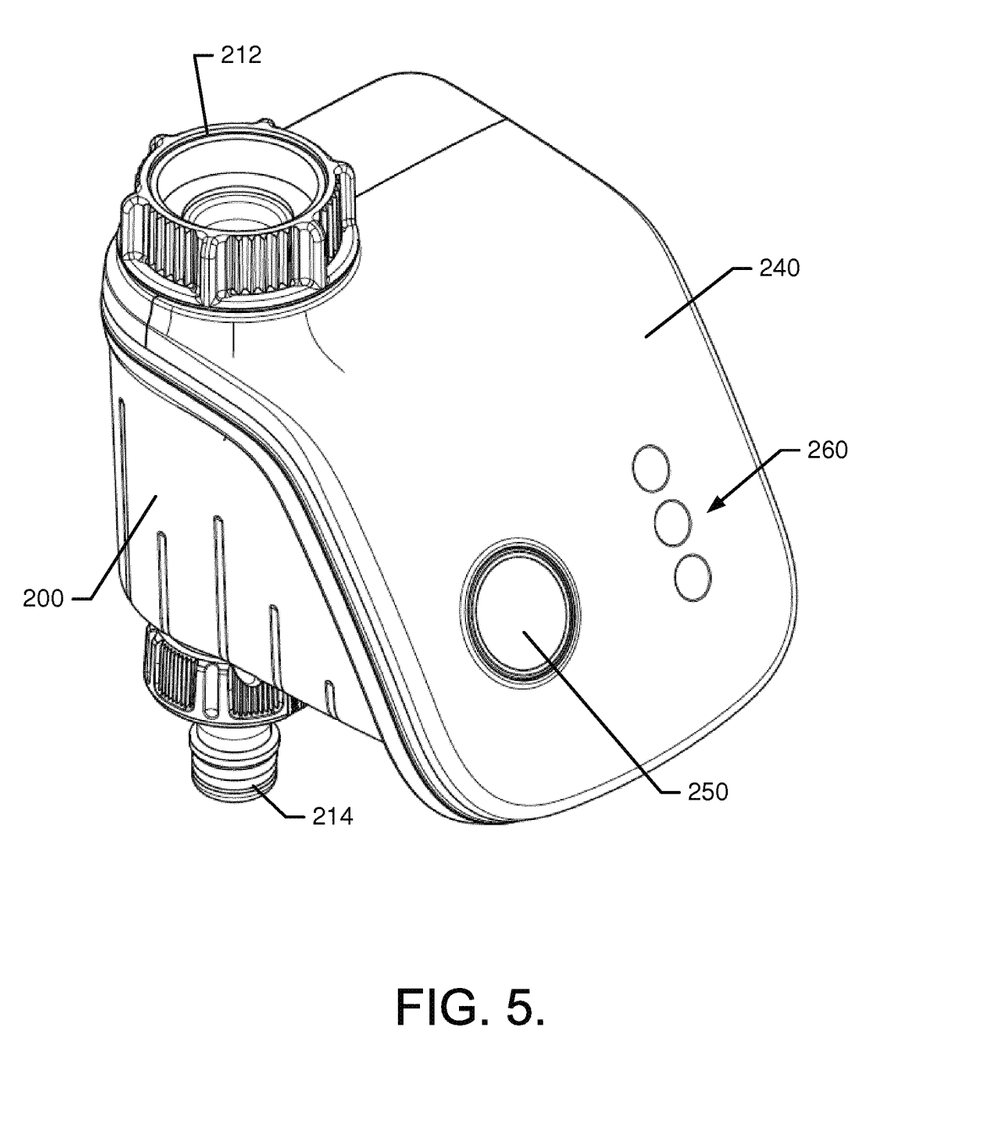
FIG. 5 illustrates a perspective view of a watering computer in accordance with an example embodiment.
Figure 6:
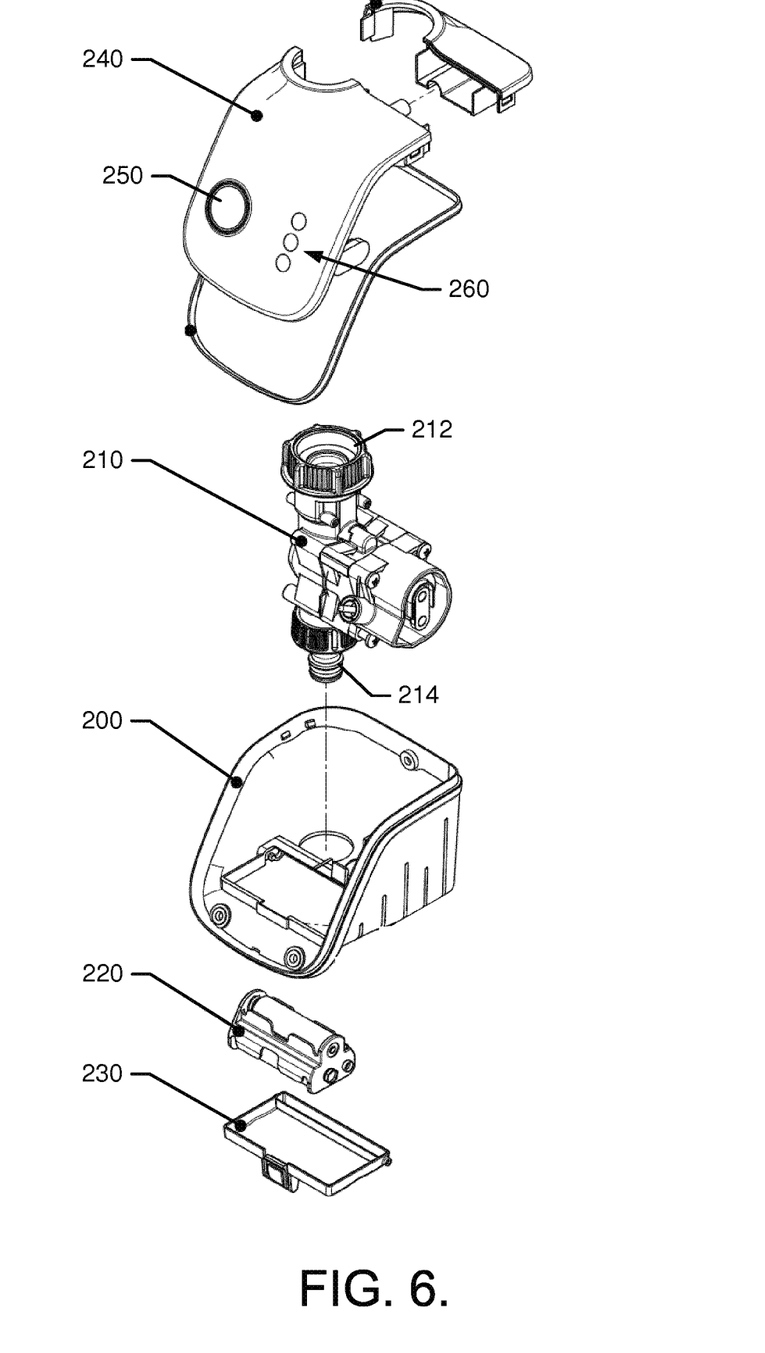
FIG. 6 illustrates an exploded perspective view of the watering computer in accordance with an example embodiment.

Although the first and second watering computers 120 and 122 could take different physical forms, an example structure for embodying a watering computer is shown in FIGS. 5 and 6. The watering computer may include a housing body 200 that houses a valve assembly 210 (which includes valve 170) and a battery pack 220 (e.g., P/S 150). The battery pack 220 may be provided in a battery compartment that is accessible via the battery compartment door 230. The valve assembly 210 may include a tap adapter 212 configured to interface with a spigot or tap of a pressurized water system (e.g., water source 100) and provide an input port for the valve assembly 210. An output port of the valve assembly 210 may include a hose adapter 214, which may include or be embodied as a quick coupler to/from which a hose can easily be connected/disconnected. The housing body 200 may mate with a cover plate 240, which may be a single plate or made of multiple plates. In an example embodiment, the cover plate 240 may include a single main button 250, which may be the only physically embodied operable member associated with the user interface of the watering computer. The other physical portion of the user interface that is local to the watering computer may be a light assembly 260, which may include one or more LEDs.

The main button 250 may have at least two functions (and in some cases only two functions). In this regard, the main button 250 may be operated to manually shift the valve assembly 210 so that the valve 170 is alternately opened or closed (i.e., changed from its current condition to the opposite condition) and/or to trigger a display of status information via the light assembly 260. In an example embodiment, if the valve 170 is closed, pressing the main button 250 will cause the light assembly 260 to show the current state of the watering computer for a predetermined amount of time (e.g., 20 seconds). After the predetermined amount of time has passed, the watering computer may shut off the light assembly 260 and the valve 170 may remain closed. If the main button 250 is pressed a second time before the predetermined amount of time has passed, the valve 170 may be opened. In some embodiments, the valve 170 may remain open for the same amount of time that the operator defined for valve opening via the app the last time the operator used the app. Thus, even for manual operation, the time for which the valve 170 remains opened is adaptive insofar as the opening time is based on programmed settings used the last time the operator interacted with the app.

Figure 7:
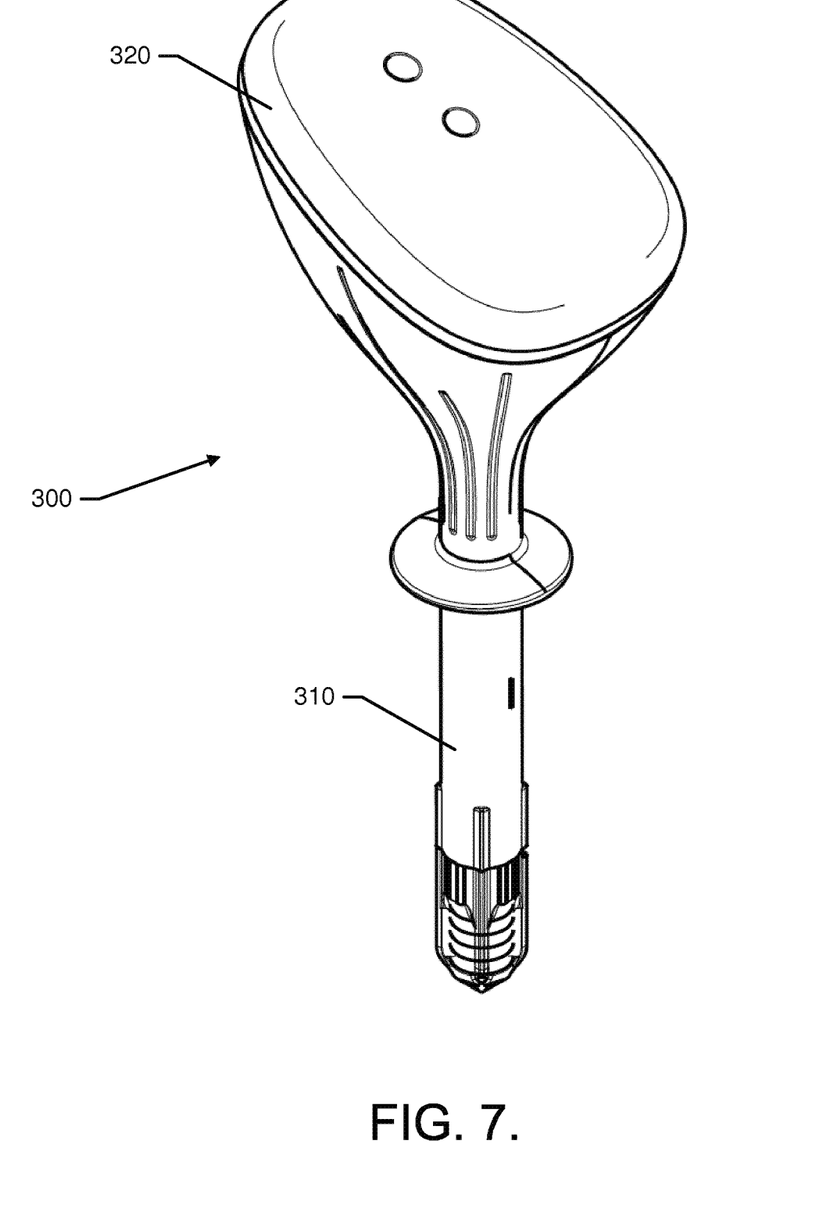
FIG. 7 illustrates a perspective view of a sensor according to an example embodiment.

FIG. 7 illustrates a perspective view of a sensor 300 according to an example embodiment. The sensor 300 may include a base portion 310, which may be inserted into the ground. The base portion 310 may be tapered to facilitate piercing the ground for placement therein. However, in some embodiments, the base portion 310 may also house sensor portions for interfacing with the ground to detect temperature, pH, moisture, and/or the like. The base portion 310 may support a head portion 320 inside which a battery compartment may be provided for supporting the battery pack that powers the sensor 300. The head portion 320 may also house communications and/or processing equipment (e.g., the C/C 160 and any antenna(s) and/or the like). In some cases, the head portion 320 may also house a light sensor or other sensing equipment.

Embodiments of the present invention may therefore be practiced using apparatuses such as those depicted in FIGS. 1-7. As such, a system of an example embodiment may include sensor equipment having one or more sensors disposed on a parcel of land, watering equipment disposed on the parcel and configured to selectively apply water to the parcel, and a gateway configured to provide for communication with the sensor equipment and the watering equipment. The gateway may interface between a first network and a second network. The first network may include at least the watering equipment and the sensor equipment. An operator may be enabled to wirelessly communicate with the gateway via the second network. At least one component of the watering equipment or the sensor equipment may be an adaptive component.

The system may further include a robotic rover that is also adaptively configured. In an example embodiment, the watering equipment may include a watering computer including a valve assembly. The watering computer may be operably coupled to a water source and a water line such that the valve assembly is operable, by the watering computer, to alternately couple the water source to and isolate the water source from the water line. In some embodiments, the sensor equipment may include a sensor paired with the watering computer via the gateway to communicate sensor data to the watering computer. In some cases, the watering computer may be adaptive as a programmable feature such that the operator is enabled to program a specific adaptive behavior as an adjustable parameter, relationship or response. In an example embodiment, the watering computer may be adaptively configured to respond to temperature by receiving temperature data and providing an alert to the operator responsive to the temperature data being within a predetermined amount of a freezing point. In some embodiments, the watering computer may be adaptively configured to respond to the sensor data by operating the valve assembly based on an indication that the sensor data corresponds to an operator selected trigger. In an example embodiment, the watering computer may be adaptively configured to respond to a loss of connectivity to the gateway or the sensor by employing a previously programmed watering schedule. In some cases, the watering computer may be adaptive as a default feature such that the watering computer employs a default parameter, relationship or response responsive to an absence of communication from the gateway. In some embodiments, the watering computer may be configured to employ a last sensor data parameter responsive to not receiving a response to a request for sensor data from the sensor. In an example embodiment, the watering computer may be configured to erase memory and restore default settings responsive to a reset condition. In some cases, the watering computer may be configured to enter a pairing mode responsive to a reset condition. In some examples, the sensor may be configured to adaptively report sensor data to the gateway. In an example embodiment, the sensor may be configured to adaptively report sensor data to the gateway by determining whether a current reading is different from a last reading by greater than a threshold amount, and may only transmit the current reading to the gateway responsive to the current reading being different from the last reading by greater than the threshold amount. In some embodiments, the second network may include a user terminal via which the operator provides a watering schedule or parameters for initiating watering based on sensor data to the watering computer. In some cases, the second network may include an in-home access point that is wirelessly connectable to the gateway, and a first wireless link that is employed on the first network may be different than a second wireless link employed on the second network. In an example embodiment, the operator may be enabled to receive battery status information or signal strength information relating to the watering equipment or the sensor equipment. In some cases, the watering computer may include a main button and a light assembly, and the main button may be manually operable to display status via the light assembly or to actuate the valve assembly. In some embodiments, the operator may be enabled to interface with the watering equipment and the sensor equipment via the gateway to pair devices of the watering equipment with corresponding devices of the sensor equipment. In an example embodiment, the operator may be enabled to interface with the watering equipment, the robotic rover and the sensor equipment via the gateway to coordinate watering and mowing schedules. In some cases, the operator may be notified via the gateway when one of the watering equipment or the robotic rover is actuated via the gateway while the other of the watering equipment or the robotic rover is operating in a same area.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

The invention claimed is:

1. A system comprising:
sensor equipment including one or more sensors disposed on a parcel of land, each of the one or more sensors comprising control circuitry configured to detect sensor data on the parcel of land;
a robotic rover comprising control circuitry configured to selectively perform mowing tasks on the parcel of land;
a watering computer comprising control circuitry configured to selectively apply the water to the parcel of land;
a gateway configured to provide for communication between the control circuitry of each of the one or more sensors of the sensor equipment, the watering computer, and the robotic rover; and
a user terminal comprising processing circuitry that is configured to communicate with the gateway,
wherein the gateway interfaces between a first network comprising the robotic rover, the watering computer, and the sensor equipment and a second network via which an operator is enabled to wirelessly communicate with the gateway via the user terminal,
wherein in response to communication between the control circuitry of the watering computer and the control circuitry of the robotic rover, schedules of the watering computer and the robotic rover are automatically coordinated, wherein mowing and watering of a same area of the parcel are not conducted at a same time.

2. The system of claim 1, wherein the watering computer comprises a valve assembly, wherein the watering computer is operably coupled to a water source and a water line such that the valve assembly is operable by the watering computer to alternately couple the water source to and isolate the water source from the water line.

3. The system of claim 2, wherein the watering computer is configured to respond to the sensor data by operating the valve assembly based on an indication that the sensor data corresponds to an operator selected trigger.

4. The system of claim 2, wherein the watering computer comprises a main button and a light assembly, and wherein the main button is manually operable to display status via the light assembly or actuate the valve assembly.

5. The system of claim 1, wherein the watering computer is adaptive as a programmable feature such that the operator is enabled to program a specific adaptive behavior as an adjustable parameter, relationship or response.

6. The system of claim 5, wherein the watering computer is configured to respond to temperature by receiving temperature data and providing a temperature alert to the operator responsive to the temperature data being within a predetermined amount of a freezing point.

7. The system of claim 1, wherein the watering computer is configured to respond to a loss of communication to the gateway or the sensor equipment or robotic rover by employing a previously programmed watering schedule.

8. The system of claim 1, wherein the watering computer is adaptive as a default feature such that the watering computer employs a default parameter, relationship or response responsive to an absence of communication from the gateway.

9. The system of claim 8, wherein the watering computer is configured to employ a last sensor data parameter responsive to not receiving a response to a request for the sensor data from the one or more sensors.

10. The system of claim 8, wherein the watering computer is configured to erase memory and restore default settings responsive to a reset condition.

11. The system of claim 8, wherein the watering computer is configured to enter a pairing mode responsive to a reset condition.

12. The system of claim 1, wherein the one or more sensors are configured to adaptively report the sensor data to the gateway by determining whether a current reading is different from a last reading by greater than a threshold amount, and only transmitting the current reading to the gateway responsive to the current reading being different from the last reading by greater than the threshold amount.

13. A system comprising:
sensor equipment including one or more sensors disposed on a parcel of land, each of the one or more sensors comprising control circuitry configured to detect sensor data of the parcel of land;
a robotic rover comprising control circuitry configured to selectively perform mowing tasks on the parcel of land;
a watering computer comprising control circuitry configured to selectively apply water to the parcel of land;
a gateway configured to provide for communication between the control circuitry of each of the one or more sensors of the sensor equipment, the watering computer, and the robotic rover; and
a user terminal comprising processing circuitry that is configured to communicate with the gateway,
wherein the gateway interfaces between a first network comprising the robotic rover, the watering computer, and the sensor equipment and a second network via which an operator is enabled to wirelessly communicate with the gateway via the user terminal,
wherein the watering computer is configured to selectively apply the water to the parcel of land based on a watering schedule and the robotic rover is configured to selectively perform the mowing task based on a mowing schedule,
wherein the processing circuitry of the user terminal is configured to automatically coordinate or de-conflict the watering schedule and the mowing schedule in response to communication between the control circuitry of the watering computer and the control circuitry of the robotic rover, wherein mowinq and wateringq of a same area of the parcel are not conducted at a same time.

14. The system of claim 13, wherein the robotic rover is configured to gather plant species data from the parcel of land, and the processing circuitry of the user terminal is configured to form the watering schedule at least in part based on growing conditions of the plant species data collected.

15. The system of claim 13, wherein in response to a modification to the watering schedule of the watering computer by the operator, the processing circuitry of the user terminal is configured to determine if the modification creates an error or a conflict with the mowing schedule.

16. The system of claim 15, wherein the user terminal is configured to provide the modification to the watering schedule.

17. The system of claim 16, wherein the gateway interfaces with the second network by connection to an access point, the access point being an in-home access point that is wirelessly connectable to the gateway, and wherein the first network provides a first wireless link and the second network provides a second wireless link for instructions from the operator, the first and second wireless links being different wireless links that employ different communication protocols or frequencies.

18. The system of claim 16, wherein the operator is enabled to receive educational content, battery status information, or signal strength information relating to the watering computer, the robotic rover, or the sensor equipment.

19. The system of claim 15, wherein in response to determining that the modification creates the error or the conflict with the mowing schedule, the processing circuitry of the user terminal is configured to cause a scheduling alert to be sent to the operator.

* * * * *